United States Patent [19]

Shoher et al.

[11] Patent Number: 4,459,112
[45] Date of Patent: Jul. 10, 1984

[54] DENTAL JACKET CROWN, COPING AND METHOD OF FORMING A CROWN

[76] Inventors: Itzhak Shoher, 50 Shlomo Hamelech St., Tel Aviv; Aharon Whiteman, 13 J1 Perez St., Petach Tikvah, both of Israel

[21] Appl. No.: 414,415

[22] Filed: Sep. 2, 1982

[51] Int. Cl.³ .......................... A61C 5/08; A61C 5/10
[52] U.S. Cl. .................................. 433/222; 433/218; 433/223
[58] Field of Search ............... 433/222, 223, 218, 227, 433/208, 207; 264/19, 20

[56] References Cited

U.S. PATENT DOCUMENTS

| | | | |
|---|---|---|---|
| 503,419 | 8/1893 | Johnston | 433/227 |
| 1,172,918 | 2/1916 | Thorp | 433/222 |
| 1,248,242 | 11/1917 | Babcock | 433/223 |
| 1,609,550 | 12/1926 | Jaques, Jr. | 433/218 |
| 1,734,676 | 11/1929 | Jaques, Jr. | 433/222 |
| 2,700,822 | 2/1955 | Infante | 433/222 |
| 4,273,580 | 6/1981 | Shoher et al. | 433/207 |

Primary Examiner—John J. Wilson

[57] ABSTRACT

The dental jacket crown of the present invention is prepared from a thin metal foil substrate which is coated with a noble based metal composition having a low fusing temperature and folded in a predetermined manner to form a multiple number of triangular like flaps or pleats. The folded foil represents the coping of the present invention. The coping is mounted over a die of the prepared tooth and the flaps wrapped in overlapping formation and then adapted to the die. The die is removed and the structure heated preferably under a bunsen burner. A veneering material such as porcelain is then coated over the structure to form the crown.

16 Claims, 5 Drawing Figures

DENTAL JACKET CROWN, COPING AND METHOD OF FORMING A CROWN

This invention relates to the field of dental restorations and more particularly to the jacket crown restoration, a jacket crown coping for a jacket crown restoration and to a method for forming a jacket crown.

Dental porcelain, a conventional material composed of a mixture of feldspar, quartz and kaolin is commonly used in fabricating dental restorations. The most prevalent crown construction for dental restorations is the porcelain veneer cast metal crown. The cast metal crown is fabricated using a relatively thick metal understructure formed from casting an investment of a wax or plastic pattern of the prepared tooth. Dental porcelain is then applied in layers over part or all of the understructure and fired at high temperature to form a veneer. The metal understructure is preferably formed from a noble based metal or alloy predominantly of gold. The thickness of the cast metal understructure ranges from typically 0.3 to 0.5 mm. The cast metal understructure is expensive and particularly so for a noble based metal understructure. The weight of a precious metal cast crown is from one to three grams. Since the bulk of the restoration is no greater than that of the tooth structure which originally occupied the space, the use of a thick metal understructure minimizes the permissible thickness for the translucent porcelain veneer. Moreover, exposure of the metal understructure will detract from the esthetics of the restoration.

It is well known that the full porcelain or porcelain jacket crown is esthetically superior to all other crown restorations and is virtually impossible to visually distinguish from a natural tooth. Accordingly, it should be commonplace but is, in general, indicated for use only as a full coverage for an anterior tooth where esthetics is the prime consideration. The limited use of the porcelain jacket crown is attributable to its present method of construction with the strength of the jacket crown dependent upon the strength of the porcelain material composition. Porcelain is inherently structurally weak and fragile. In addition, the present day method of construction requires a high degree of proficiency to establish accurate marginal fit and finish and to avoid poor seating of the crown occlusally relative to the preparation. An improper fit at the gingival margin results in a cement line which readily washes away inviting decay and loosening the crown attachment.

In the conventional process for preparing a porcelain jacket crown a platinum foil is swaged about the prepared die of the tooth to form a mold substrate upon which the porcelain may be fired. The foil is then removed from the substrate before the crown is cemented to the tooth preparation. The latter requirement is considered a principle failing of the conventional porcelain jacket crown preparation. An improved porcelain jacket crown construction in which the swaged foil substrate is itself included as an integral component of the finished porcelain jacket crown is taught and described in U.S. Pat. No. 4,273, 580 issued to the Applicants herein, the disclosure of which is herein incorporated by reference. In the latter patent the metal foil substrate forms the core of the jacket crown. A coating of a predetermined noble based metal composition is sintered to the foil substrate which is then adapted to the die in a manner similar to that in the conventional preparation of a porcelain jacket crown. Although this jacket crown construction will exhibit substantially improved physical properties, its method of construction is still dependent upon the skill and dexterity of a superior dental technician.

The present invention utilizes an entirely new technique for constructing a porcelain jacket crown which overcomes all of the shortcomings of the conventional porcelain jacket crown in mechanical properties, construction and preparation. In fact the preformed coping of the present invention is readily adaptable by a technical novice without any special skills. Use of the preformed coping in accordance with the present invention simplifies construction of a porcelain jacket crown and significantly contributes to uniformity in result without the dependency on the skill of the dental technician.

The porcelain jacket crown of the present invention may be prepared more quickly and more accurately relative to conventional methods of preparation. Moreover, the dental laboratory does not have to wax, invest, cast or polish the final metal structure as is done in making a porcelain veneer cast metal crown.

In addition, the present invention may be used with any conventional tooth margin preparations such as: chamfer, shoulder, chamfer bevel, shoulder bevel, knife edge and feather edge. The margin may also be reinforced if desired. The porcelain jacket crown prepared in accordance with the present invention will have an almost invisible metal line at the gingiva. An even further distinct advantage of the present invention lies in the reduction in the weight of the metal in a jacket crown of the present invention which is only 20 to 30 milligrams.

Accordingly, it is the principle object of the present invention to provide a porcelain jacket crown having a high resistance to fracture comparable with or even greater than the conventional porcelain veneer cast metal crown.

Another object of the present invention is to provide a preformed coping for forming the porcelain jacket crown of the present invention.

An even further object of the present invention is to provide a method for constructing a jacket crown.

Further objects and advantages of the present invention will become apparent from the following detailed description of the invention when read in conjunction with the accompanying drawings of which:

Figure 1:
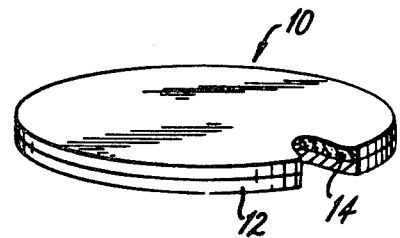
FIG. 1 is an enlarged perspective of a segment of the preferred metal foil starting material of the present invention in its preferred circular geometry.

Referring now to FIG. 1 in which a metal foil segment 10 is shown representing the starting material for preparing the jacket crown in accordance with the present invention. The metal foil segment 10 is preferably circular in geometry and composed of a thin foil metal substrate 12 of platinum or another high fusing temperature metal and a thin coated layer 14 superimposed on the foil metal substrate 12. The coated layer 14 should be of a noble metal based composition preferably with gold as its major constituent. There are numerous gold based compositions known to those skilled in the dental arts for use in the preparation of a dental restoration and upon which a veneering material such as porcelain may be fired. The preferred composition of the coated layer 14 should have a relatively low melting temperature characteristic and contain at least 50% gold with one or more of the following elements in combination: silver, palladium, platinum, iridium, copper and aluminum. A conventional binder may be added to the composition so that it may spread more readily over the platinum foil substrate 12 to form the coated layer 14. The coated layer 14 should form a bonded matrix with or without the application of heat which has the physical properties of being flexible, malleable and spongy. The gold based composition should have a low temperature fusing characteristic such that it flows after sufficient heat is applied for reasons which will be explained in greater detail hereafter.

The thickness of the platinum foil substrate 12 should be in the range of between 15 to 50 microns with an optimum thickness of 25 to 27 microns. The thickness of the gold based layer 14 should be between 10 to 50 microns and preferably between 20 to 25 microns.

The metal foil segment 10 is preferably round although any geometry may be used in which multiple folds may be made which will partially overlap one another when adapted to a die as hereafter explained. When the metal foil segment 10 is circular its diameter for a typical die is between about 22 to 28 mm.

Figure 2:
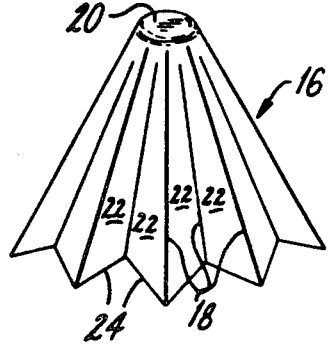
FIG. 2 is a perspective of a dental coping prepared in accordance with the present invention from the metal foil starting material of FIG. 1.

The metal foil segment 10 of FIG. 1 is folded into a predetermined geometrical shape having a multiple number of fold lines 18 as shown in FIG. 2 for forming the dental coping 16 of the present invention. The multiple fold lines 18 may be formed by hand or by machine. The technique or mechanism employed to perform the folding operation is not critical to the present invention. It is the arrangement of multiple fold lines in a predetermined array to form multiple flaps or pleats which forms the underlying theory in the preparation of a jacket crown in accordance with the present invention.

An example of a hand folding operation that may be used for forming a preferred arrangement of fold lines 18 from the metal foil segment 10 involves placing the metal foil segment 10 over one end of a cylindrical support bar (not shown) and squeezing the segment 10 into fold lines 18 using the thumb and forefinger of one hand while holding the segment 10 in place over the support bar. In such case each fold line 18 will radially extend from a central unfolded area 20. The central unfolded area 20 will conform in dimension to the support bar upon which it was placed in forming the fold lines 18. The diameter of the unfolded area is not significant provided it is small relative to the total area of the segment 10.

Another hand folding operation simply involves folding the segment 10 in half and then in quarters until the desired number of fold lines 18 are formed. This is a somewhat less desirable procedure since the fold lines will extend radially from a central point or apex without forming an unfolded area 20 in the center of the segment 10. It should however be understood that forming an unfolded area 20 is not critical to the invention.

Figure 3:
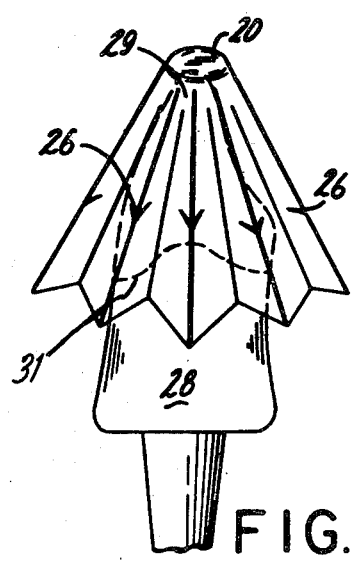
FIG. 3 is a transparency in perspective of the dental coping of FIG. 2 in the initial stage of being molded to a die of the prepared tooth.

The fold lines 18 form substantially triangular like flaps or pleats 22 with a curved base line 24 shown as a straight line in FIGS. 2 and 3 for simplicity. Each triangular like flap 22 has two fold lines 18 with a common fold line 18 between adjacent pairs. The number of flaps 22 that should be formed may vary with four to sixteen being preferred and with eight being the optimum number for most typical jacket crown preparations.

The preferred geometry of the dental coping 16 includes a multiple number of fold lines 18 which radially extend from a centrally located unfolded area 20 in an arrangement which form triangular-like flaps 22. The dental coping 16 should preferaly be modified to include a plurality of small slotted openings 26. These openings 26 may be made as an integral part of the manufacturing operation of the dental coping 16 or as part of the procedure of the dental technician in the preparation of the jacket crown as will hereinafter be explained in greater detail. The slotted openings 26 are slits formed in the segment 10 preferably along the fold lines 18. Neither the position of the slotted openings 26, their size or number are critical. Their primary function is to provide access for the noble metal composition to flow to the underside or uncoated surface of the platinum foil substrate 12 when heat is applied to the finished coping 16 during the final preparatory step in the preparation of a jacket crown.

FIG. 3–6 illustrate the preferred sequence of steps in the preparation of a jacket crown in accordance with the present invention. The preformed coping 16 is placed over a die 28 of a prepared tooth with the unfolded area 20 seated upon the top or occlusal end 29 of the die 28. The die 28 is conventionally prepared from an impression of the prepared tooth and is a replica thereof. The unfolded area 20 facilitates centering the dental coping 16 over the die 28 and makes the coping 16 easier to adapt to the die 28 as is more readily apparent from FIG. 4.

Figure 5:
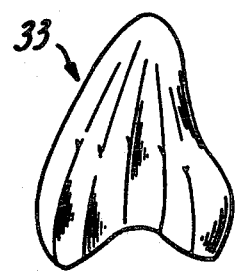
FIG. 5 is an illustration in perspective of the dental coping of FIG. 3 as a free standing structure after having been adapted to the die.
Figure 4:
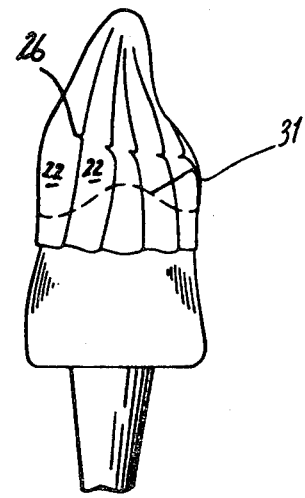
FIG. 4 is another transparency in perspective of the dental coping in FIG. 3 in its final stages of being adapted to the die of the prepared tooth.

Each of the flaps 22 are wrapped tightly around the die 28 in a uniform clockwise or counter clockwise oriented sequence resulting in an arrangement of overlapping flaps 22 as shown in FIG. 4. The coping 16 should also extend over the gingival margin 31. The die 28 and coping 16 is then placed in a swaging device (not shown) or pressure is applied by hand to adapt it to the die 28. The coping 16 is then removed from the die leaving a free standing structure 33 as shown in FIG. 5. Heat is then applied to the free standing structure 33 by placing it over the flame of a bunsen burner for between five to thirty seconds based on flame temperature until the structure 33 gets cherry red and shiny. Alternatively the free standing structure 33 can be placed in a furnace and sintered at a temperature of about 1020° to 1070° C. until the same result is achieved. The low fusing preferably gold based composition of the metal layer 14 will flow through the slotted openings 26 to form a compact matrix between the foil substrate 12 and the gold based composition on the undesirable thereof without any air pockets.

After the heating step, porcelain can be directly applied in a conventional manner to form the jacket crown of the invention. It is however desirable but not essential, to coat the outside surface of the free standing foil structure 33 using a bonding composition to achieve an unbreakable bond between the porcelain layers and the foil structure 33. A preferred bonding composition is disclosed in a copending U.S. patent application Ser. No. 171,255 entitled Bonding Material and Method For Bonding A Ceramic To A Nobel Based Metal, and now abandoned, the disclosure of which is herein incorporated by reference. The bonding material disclosed in this application includes a nobel based metal composition in combination with a halide of a noble metal preferably a noble metal halide. The bonding material must be sintered to the foil structure 33 at a temperature above 1600° F. This can be achieved simultaneously with the firing of the required porcelain outer layers. Any number of porcelain layers may be applied and fired for forming the jacket crown of the invention. Generally, three or more layers of varying dental porcelain composition starting with an opaque layer are built up and fired at temperatures in a range from about 1600° to 1820° F. Before firing the final glaze the area below the gingival margin is cut and the porcelain shaped and finished to the correct gingival margin for the prepared tooth.

After the final glaze the crown is ready to be inserted into the mouth and cemented to the tooth using any conventional dental cement composition. It is suggested practice to roughen the interior of the crown i.e. the unerside of the inner substrate layer 12 before the crown is cemented to the tooth. The roughness may be achieved by sandblasting.

Although the invention was described in connection with the application of porcelain for forming a porcelain jacket crown it is equally applicable to the use of any polymer veneering material such as conventional dental acrylics in substitution of the porcelain ceramic material for the superstructure of the jacket crown.

What we claim is:

1. A jacket crown comprising a composite body including a thin foil of high fusing temperature metal having a surface geometry conforming to a die to which it has been adapted with the foil having at least a minimum of three folded over pleats with each pleat forming a triangular like flap in the unfolded position, a thin coating of a noble based metal composition superimposed over one surface of said thin metal foil and disposed beneath the folded over pleats and a relatively thick outer coating of a dental veneering material.

2. A jacket crown as defined in claim 1 wherein said folded over pleats overlap one another.

3. A jacket crown as claimed in claim 2 wherein said thin foil is composed of platinum and wherein said veneering material is fired on dental porcelain.

4. A jacket crown as claimed in claim 2 wherein said noble based metal composition comprises at least 50% gold and at least one of the following elements selected from the group consisting of: silver, palladium, iridium, copper and aluminum.

5. A jacket crown as claimed in claim 4 wherein the weight of said noble based metal in said jacket crown is between about 20 to 30 milligrams.

6. A dental coping for a jacket crown restoration comprising a thin foil of high fusing temperature metal arranged in a prefolded geometrical configuration having at least a minimum of three pleated sections with each pleated section represented by fold lines which form a triangular like flap and a coating of a noble based metal composition superimposed upon the surface of said thin foil over said pleated sections.

7. A dental coping as defined in claim 6 wherein each pleated section is of a size such that upon folding it will overlap an adjacent pleated section.

8. A dental coping as defined in claim 7 wherein said thin foil was circular in shape before folding;

9. A dental coping as defined in claim 8 wherein said fold lines radially extend from an unfolded area substantially in the center of said coping with the unfolded area being small compared to the total area of the foil.

10. A dental coping as defined in claim 9 wherein said thin foil is composed of platinum.

11. A dental coping as defined in claim 10 further comprising a plurality of small slotted openings arranged about the periphery of said coping.

12. A method of forming a dental jacket crown comprising
preparing a thin metal foil of high fusing temperature metal into a substantially circular substrate;
coating one surface of the foil substrate with a noble based metal composition having a low fusing temperature of below about 1070° C.;
forming a multiple number of fold lines in said coated foil substrate with each two adjacent fold lines substantially defining a triangular like flap;
mounting said coated foil substrate over a die of the prepared tooth with the coated surface exposed;
partially overlapping each flap about said die in a clockwise or counterclockwise sequence with the foil tightly wrapped about said die;
adapting said tightly wrapped foil to said die;
removing said die for providing an inner structure for said jacket crown;
heating said inner structure above the low fusing temperature of said noble based metal composition; and
coating a veneering material over said inner structure.

13. A method as claimed in claim 12 further comprising the step of forming small slotted openings about the periphery of said coated foil substrate following the folding step.

14. A method as claimed in claim 13 wherein said slotted openings are formed along the fold lines.

15. A method as claimed in claim 14 wherein said veneering material is a fired on porcelain.

16. A method as claimed in claim 15 wherein said heating step is performed by placing said inner structure under the flame of a bunsen burner for between 5 to about 30 seconds.

* * * * *